United States Patent
Prencipe et al.

(10) Patent No.: US 11,628,128 B2
(45) Date of Patent: *Apr. 18, 2023

(54) ORAL CARE COMPOSITION

(71) Applicant: Colgate-Palmolive Company, New York, NY (US)

(72) Inventors: Michael Prencipe, West Windsor, NJ (US); Andre Morgan, Robbinsville, NJ (US); Venda Porter-Maloney, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 431 days.

This patent is subject to a terminal disclaimer.

(21) Appl. No.: 15/849,129

(22) Filed: Dec. 20, 2017

(65) Prior Publication Data

US 2018/0116924 A1    May 3, 2018

Related U.S. Application Data

(63) Continuation of application No. 15/365,889, filed on Nov. 30, 2016, now Pat. No. 9,883,995, which is a continuation of application No. 14/147,826, filed on Jan. 6, 2014, now Pat. No. 9,532,932, which is a continuation of application No. 13/637,370, filed as application No. PCT/US2010/029472 on Mar. 31, 2010, now Pat. No. 8,652,495.

(51) Int. Cl.
| | | |
|---|---|---|
| *A61K 8/27* | (2006.01) | |
| *A61K 8/44* | (2006.01) | |
| *A61K 8/73* | (2006.01) | |
| *A61Q 11/00* | (2006.01) | |
| *A61K 8/02* | (2006.01) | |
| *A61K 8/19* | (2006.01) | |
| *A61K 8/29* | (2006.01) | |

(52) U.S. Cl.
CPC .............. *A61K 8/27* (2013.01); *A61K 8/0245* (2013.01); *A61K 8/19* (2013.01); *A61K 8/29* (2013.01); *A61K 8/44* (2013.01); *A61K 8/731* (2013.01); *A61Q 11/00* (2013.01); *A61K 2800/412* (2013.01); *A61K 2800/594* (2013.01); *A61K 2800/5922* (2013.01); *A61K 2800/624* (2013.01)

(58) Field of Classification Search
CPC .......... A61K 8/27; A61K 8/0245; A61K 8/19; A61K 8/29; A61K 8/44; A61K 8/731; A61K 2800/412; A61K 2800/5922; A61K 2800/594; A61K 2800/624; A61Q 11/00
See application file for complete search history.

(56) References Cited

U.S. PATENT DOCUMENTS

| | | | |
|---|---|---|---|
| 3,538,230 A | 11/1970 | Pader et al. | |
| 3,966,863 A | 6/1976 | Forward et al. | |
| 3,980,767 A | 9/1976 | Chown et al. | |
| 4,187,288 A | 2/1980 | Cordon et al. | |
| 4,328,205 A | 5/1982 | Taylor | |
| 4,358,437 A | 11/1982 | Duke | |
| 4,992,259 A | 2/1991 | Schiraldi et al. | |
| 5,330,748 A | 7/1994 | Winston et al. | |
| 5,370,865 A | 12/1994 | Yamagishi et al. | |
| 5,385,727 A | 1/1995 | Winston .................... A61K 8/19 424/49 |
| 5,455,024 A | 10/1995 | Winston et al. | |
| 6,197,343 B1* | 3/2001 | Minami ............... A61K 8/0283 424/401 |
| 6,287,541 B1 | 9/2001 | Creeth et al. | |
| 6,558,710 B1 | 5/2003 | Godfrey | |
| 6,669,929 B1 | 12/2003 | Boyd et al. | |
| 8,652,495 B2* | 2/2014 | Porter ...................... A61K 8/27 424/401 |
| 9,532,932 B2* | 1/2017 | Prencipe .................. A61K 8/27 |
| 9,883,995 B2* | 2/2018 | Prencipe .................. A61K 8/27 |
| 2003/0133900 A1* | 7/2003 | McLaughlin .......... A61K 8/361 424/70.22 |
| 2004/0241252 A1 | 12/2004 | Abney et al. | |
| 2005/0175552 A1 | 8/2005 | Hoic et al. | |
| 2006/0024246 A1 | 2/2006 | Maitra et al. | |
| 2007/0020201 A1 | 1/2007 | Boyd et al. | |
| 2007/0104660 A1 | 5/2007 | Miksa et al. | |
| 2007/0166243 A1 | 7/2007 | Yoshida et al. | |
| 2007/0196349 A1* | 8/2007 | Kitamura ............... A61K 8/355 424/94.1 |
| 2008/0160093 A1 | 7/2008 | Schwartz et al. | |
| 2009/0186090 A1 | 7/2009 | Zaidel et al. | |
| 2009/0202451 A1 | 8/2009 | Prencipe et al. | |
| 2009/0202454 A1 | 8/2009 | Prencipe et al. | |
| 2009/0202455 A1 | 8/2009 | Kohli et al. | |

FOREIGN PATENT DOCUMENTS

| | | |
|---|---|---|
| CN | 1519227 | 8/2004 |
| DE | 102006046952 | 4/2008 |
| GB | 2052978 | 2/1981 |
| GB | 2354441 | 3/2001 |
| GB | 2354441 A | 3/2001 |
| JP | 08-073816 | 3/1996 |
| JP | 2006-131522 | 5/2006 |
| JP | 2010-037293 | 2/2010 |
| RU | 2139034 | 10/1999 |

(Continued)

OTHER PUBLICATIONS

Gan, S.Y. et al., "Antibacterial Activity of Zn-chelator Complexes," presented at IADR/AADR/CADR 87th General Session and Exhibition (Apr. 1-4, 2009).

(Continued)

*Primary Examiner* — Ali Soroush

(57) ABSTRACT

Disclosed are oral care compositions, for example dentifrice compositions, comprising an oral care composition comprising an orally acceptable vehicle, metal oxide particles having an average particle size of no greater than a dentin tubule and at least one amino acid capable of chelating the metal oxide. The composition may comprise a polymeric adherent material for adhering the metal oxide particles in the dentin tubule. The metal oxide particles have a median particle size of 5 microns or less, and may comprise zinc oxide.

18 Claims, 1 Drawing Sheet

(56) References Cited

FOREIGN PATENT DOCUMENTS

| | | |
|---|---|---|
| WO | WO 94/14406 | 7/1994 |
| WO | WO 00/59460 | 10/2000 |
| WO | WO 02/051945 | 7/2002 |
| WO | WO 07/076001 | 7/2007 |
| WO | WO 2008/122578 | 10/2008 |
| WO | WO 09/060385 | 5/2009 |
| WO | WO 2009/095423 | 8/2009 |

OTHER PUBLICATIONS

Müller, B. et al., "The Effect of pH on the Corrosion Inhibition of Zinc Pigments by Phenol Derivatives," Corrosion Science, 1996, vol. 38, No. 11, pp. 1869-1875.
International Search Report for International Application No. PCT/US2010/029465, dated Feb. 8, 2011.
International Search Report for corresponding International Application No. PCT/US2010/029472, dated Feb. 8, 2011.

\* cited by examiner

| Formula | Untreated | 7X brushing cycles | 12X, cola |
|---|---|---|---|
| Comparative Example 3<br><br>1wt% ZnO Powder + no amino acid | | | |
| Example 3<br><br>1wt% ZnO Powder + 3wt% L-arginine | | | |

ORAL CARE COMPOSITION

CROSS-REFERENCE TO RELATED APPLICATIONS

This application is a continuation of U.S. application Ser. No. 14/147,826, filed Jan. 6, 2014, which is a continuation of U.S. application Ser. No. 13/637,370, filed on Sep. 26, 2012, which is a national stage entry under 35 U.S.C. § 371 of International Patent Application No. PCT/US2010/029472, filed on Mar. 31, 2010, which are both hereby incorporated by reference in their entireties.

The present invention relates to an oral care composition, for example a dentifrice composition, for enhanced delivery of an antiplaque/anticalculus agent to the oral surfaces in the oral cavity, and which may additionally treat or prevent hypersensitivity of the teeth. The present invention also relates to a method of delivering an antiplaque/anticalculus agent to the oral surfaces in the oral cavity and simultaneously treating or preventing hypersensitivity of the teeth. The present invention has particular application in treating or preventing hypersensitivity of the teeth by occluding dentin tubules.

BACKGROUND

Dentin is a portion of the tooth internal to the enamel and cementum that has a radially striated appearance owing to a large number of fine canals or tubules known as the dentinal tubules. Tubules run from the pulp cavity to the periphery of the dentin and are generally about two microns in diameter at their base and somewhat narrower at their periphery. Tubules are not usually exposed to the environment in the oral cavity, as they are usually covered by enamel or cementum. The cementum in turn is often covered by the gums.

It is commonly understood that partially or fully exposed tubules can lead to tooth sensitivity, an irritating and painful condition. In this theory, recession of the gum line exposes cementum to erosion. The eroded cementum in turn exposes the hollow dentinal tubules. The exposed tubules cause nerves within the tooth to be affected excessively by external oral stimuli because material and energy transfer between the exterior and interior of the tooth is accelerated through the tubules. Common environmental stimuli, such as heat, cold, chemicals and physical and mechanical pressure or stimuli, such as brushing, are able to irritate the nerve through the open dentin tubules and thereby create pain. The pain of sensitive teeth appears to result from these stimuli, which apparently cause fluid movements in the dentinal tubules that activate pulpal nerve endings.

Conventionally, two approaches have been taken to treat or ameliorate tooth sensitivity. Under one approach, the chemical environment proximal to the nerve is altered by application of various agents, such that the nerve is not stimulated, or not stimulated as greatly. Known agents useful in this chemical approach, including potassium salts (such as potassium nitrate, potassium bicarbonate, potassium chloride) and strontium, zinc salts, and chloride salts.

The second approach involves the mechanical shield of the nerve by, e.g., blocking of the dentinal tubules wholly or partially with "tubule blocking agents." Agents that have been disclosed in the prior art include, e.g., cationic alumina, clays, water-soluble or water-swellable polyelectrolytes, oxalates, amorphous calcium phosphate, hydroxyapatite, maleic acid copolymers and polyethylene particles.

US-A1-2009/0186090 in the name of the present Applicant discloses the provision of an oral care composition that reduces and/or eliminates the perception of tooth sensitivity. The composition includes an adherent material and includes, in part, silica particles having a particle size of 2-5 microns.

However, even though such an oral care composition provides clinical hypersensitivity relief, there is nevertheless still a need in the art for an oral care composition, in particular a dentifrice, that, upon use, provides enhanced prevention or reduction of tooth sensitivity and is not associated with significant processing or formulation disadvantages.

It is also known is the art to use zinc oxide as an antiplaque/anticalculus agent. It is also known to use complexes of divalent or trivalent metal ions as antiplaque agents.

It has been demonstrated in the literature that the solubility of zinc can be improved by forming a complex with a chelating molecule such as ethylenediamine tetraacetic acid or a bioactive molecule such as a cyclic alpha-hydroxyketone. For example, as disclosed in U.S. Pat. No. 6,287,541, specific cyclic alpha-hydroxyketones are used as complexing agents for divalent copper, zinc, iron or tin and trivalent iron S. Y. Gan, et al. "Antibacterial Activity of Zn-chelator Complexes." IADR. March 2009 discloses the use of inert biocompatible chelators for zinc.

However, increased solubility does not guarantee an increase in anti-plaque, anti-gingivitis, hypersensitivity, and/or fresh breath efficacy. To provide these benefits the zinc must be delivered to the hard and/or soft tissues in the oral cavity.

There is still a need for enhanced delivery of antiplaque/anticalculus agents to the oral surfaces, in particular hard and/or soft tissue in the oral cavity.

SUMMARY

In some embodiments, the present invention provides an oral care composition comprising an orally acceptable vehicle, a source of metal oxide particles having an average particle size of no greater than a dentin tubule and at least one amino acid. In some embodiments, at least one of said one or more amino acids is capable of chelating the metal oxide particles.

In some embodiments, the metal oxide particles may have an average particle size of from 1 to 7 microns. In some embodiments, the metal oxide particles have an average particle size of 5 microns or less.

The metal oxide typically comprises at least one metal oxide selected from zinc oxide, stannous oxide, titanium oxide, calcium oxide, copper oxide and iron oxide or a mixture thereof.

In other embodiments, the metal oxide is zinc oxide.

The metal oxide particles may have a particle size distribution of 3 to 4 microns, a particle size distribution of 5 to 7 microns, a particle size distribution of 3 to 5 microns, a particle size distribution of 2 to 5 microns, or a particle size distribution of 2 to 4 microns.

The metal oxide particles may be present in an amount of up to 5% by weight, based on the total weight of the oral care composition, for example in an amount of from 0.5 to 2% by weight, being based on the total weight of the oral care composition.

The metal oxide may be incorporated into the oral care composition in at least one form selected from a powder, a nanoparticle solution or suspension, or encapsulated in a polymer or bead.

Preferably, the at least one amino acid is selected from arginine, L-arginine, cysteine, leucine, isoleucine, lysine, L-lysine, alanine, asparagine, aspartate, phenylalanine, glutamate, glutamic acid, threonine, glutamine, tryptophan, glycine, valine, proline, serine, tyrosine, and histidine, and mixtures thereof.

Typically, the at least one amino acid is selected from L-arginine, cysteine, isoleucine, L-lysine, glutamic acid, serine, and mixtures thereof.

More typically, the at least one amino acid comprises L-arginine.

Optionally, the at least one amino acid is present in an amount of up to 5% by weight, further optionally from 0.5 to 5% by weight, still further optionally from 2.5 to 4.5% by weight, based on the total weight of the oral care composition.

The oral care composition may further comprise a polymeric adherent material for adhering the metal oxide particles in the dentin tubule.

In some embodiments, the metal oxide is encapsulated in a polymeric adherent material.

In some embodiments, the polymeric adherent material comprises at least one cellulose polymer.

The at least one cellulose polymer may be one or more hydroxyalkyl cellulose polymer selected from hydroxypropylmethyl cellulose (HPMC), hydroxyethylpropyl cellulose (HEPC), hydroxybutylmethyl cellulose (HBMC), and carboxymethyl cellulose (CMC).

Typically, the polymeric adherent material comprises a mixture of two hydroxyalkyl cellulose polymers having different molecular weight and the metal oxide comprises zinc oxide which is encapsulated in the mixture of two hydroxyalkyl cellulose polymers.

In other embodiments, the polymeric adherent material comprises at least one polymer selected from include poly(ethylene oxide) polymers, linear polyvinylpyrrolidone (PVP) and cross-linked polyvinylpyrrolidone (PVP), polyethylene glycol (PEG)/polypropylene glycol (PPG) copolymer, ethylene oxide (EO)-propylene oxide (PO) block copolymers, ester gum, shellac, pressure sensitive silicone adhesives, methacrylates, or mixtures thereof.

Preferably, the oral care composition is a dentifrice composition, such as a toothpaste or a gel.

Alternatively, the oral care composition is formulated into a form selected from a mouth rinse, a gum, a dissolvable lozenge, and a dissolvable film.

The present invention further provides a method of reducing dental sensitivity comprising applying to the surface of a mammalian tooth an oral care composition of the present invention.

The present invention yet further provides a method of protecting dental surfaces from acid-mediated degradation, comprising applying to the surface of a mammalian tooth an oral care composition of the present invention.

The present invention still further provides a method of maintaining or increasing the systemic health of a mammal comprising applying a composition to an oral surface of a mammal at least once a day for a duration of time, wherein the composition comprises:
a. an oral care composition of the present invention, and
b. an agent selected from triclosan; triclosan monophosphate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4ethylpyridinium chloride (TDEPC); octenidine; delmopinol; octapinol; nisin; zinc ion agent; copper ion agent; essential oils; furanones; bacteriocins, ethyllauroyl arginate, extracts of magnolia, a metal ion source, fluoride, stannous ions, arginine bicarbonate, honokiol, magonol, ursolic acid, ursic acid, morin, extract of sea buckthorn, a peroxide, an enzyme, a Camellia extract, a flavonoid, a flavan, halogenated diphenyl ether, creative, and propolis.

The present invention also provides a method of occluding a dentin tubule within the surface of a mammalian tooth comprising applying to the tooth surface a composition according to the present invention.

The compositions may contain additional therapeutic and non-therapeutic components, and may also be utilized in the practice of various methods, all of which are included within the scope of the invention. The composition and methods within the scope of the invention may be useful in, for example, reducing or eliminating tooth sensitivity of a mammal, improving/maintaining systemic health, and/or occluding dentin tubules.

The present invention is predicated on the finding by the present inventors that charged amino acids and peptides have an affinity for the soft and/or hard tissue in the oral cavity and are also capable of chelating a metal oxide, such as zinc oxide, stannous oxide, or copper oxide, which has antiplaque/anticalculus efficacy when present in a therapeutically effective amount. Upon introduction of such a complex into the oral cavity, for example by brushing of the teeth, the amino acid/peptide can act to deliver the metal oxide to the desired location in the mouth. For example, if zinc oxide is delivered to dentin, the zinc oxide amino acid complex can occlude dentin tubules and provide hypersensitivity relief. Yet further the metal oxide can provide antiplaque/anticalculus treatment or prevention.

The present inventors have found in particular that the delivery of zinc oxide from dentifrice to a hydroxyapatite surface can be increased with the addition of an amino acid such as L-arginine. The form of the zinc oxide in the dentifrice can include, but is not limited to, powder, nanoparticle solution, and encapsulation of the zinc oxide by a polymer film or bead.

BRIEF DESCRIPTION OF THE DRAWINGS

FIG. 1 depicts a comparison of the occlusion incidence resulting from treating a mammalian tooth dentin substrate with an Example of an oral care composition of the invention versus a Comparative Example, the substrates being shown untreated, after treatment by brushing, and after treatment by a first acid challenge.

DETAILED DESCRIPTION

It should be understood that the detailed description and specific examples, while indicating embodiments of the invention, are intended for purposes of illustration only and are not intended to limit the scope of the invention.

The following definitions and non-limiting guidelines must be considered in reviewing the description of this invention set forth herein. The headings (such as "Background of the Invention" and "Summary,") and sub-headings (such as "Compositions") used herein are intended only for general organization of topics within the disclosure of the invention, and are not intended to limit the disclosure of the invention or any aspect thereof. In particular, subject matter disclosed in the "Background of the Invention" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Background of the Invention is intended merely to provide a general summary of assertions made by the authors of the references, and does not constitute an admission as to the accuracy of the content of such references. Each and every reference cited herein is hereby incorporated by reference in its entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In addition, the compositions and the methods may comprise, consist essentially of, or consist of the elements described therein.

As used herein, the word "include," and its variants, is intended to be non-limiting, such that recitation of items in a list is not to the exclusion of other like items that may also be useful in the materials, compositions, devices, and methods of this invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

The invention described herein includes an oral care composition that contains at least (a) an amino acid and (b) a metal oxide particle. The metal oxide particle may have an average particle size of no greater than a dentin tubule, or alternatively it may have a median particle size of 5 microns or less.

In some embodiments, the oral care composition comprises at least one amino acid capable of chelating the metal oxide. The at least one amino acid may be selected from arginine, L-arginine, cysteine, leucine, isoleucine, lysine, L-lysine, alanine, asparagine, aspartate, phenylalanine, glutamate, glutamic acid, threonine, glutamine, tryptophan, glycine, valine, praline, serine, tyrosine, and histidine, and mixtures thereof.

Typically, the at least one amino acid is selected from L-arginine, cysteine, isoleucine, L-lysine, glutamic acid, serine, and mixtures thereof.

More typically, the at least one amino acid comprises L-arginine.

The at least one amino acid is present in an amount sufficient effectively to chelate the metal oxide, and typically may be present in an amount of up to 5% by weight, further optionally from 0.5 to 5% by weight, still further optionally from 2.5 to 4.5% by weight, based on the total weight of the oral care composition.

Metal Oxide Particles

The metal oxide particles may be present in an amount of up to 5% by weight, preferably of up to 2% by weight, more preferably from 0.5 to 2% by weight, still more preferably from 1 to 2% by weight, the weight being based on the total weight of the oral care composition.

The metal oxide may comprise one or more metal oxides selected from zinc oxide, stannous oxide, titanium oxide, calcium oxide, copper oxide and iron oxide. Mixtures of such metal oxides may be used. However, zinc oxide is most preferred. Zinc oxide is known in the art to act as an antiplaque and anticalculus agent when used in oral care compositions. Accordingly, when zinc oxide is used in the oral care compositions of preferred embodiments of the present invention, the zinc oxide may exhibit a dual function, namely occlusion of dentin tubules and providing an antiplaque/anticalculus effect.

In some embodiments, the source of metal oxide particles is selected from a powder, a nanoparticle solution or suspension, a capsule and a bead.

Therefore the embodiments of the invention include metal oxide, preferably zinc oxide, particles of a particular particle size, the particle size being selected to achieve occlusion of dentin particles.

Particle Size and Distribution

In this specification, particle size distribution was measured using a Malvern Particle Size Analyzer, Model Mastersizer 2000 (or comparable model) (Malvern Instruments, Inc., Southborough, Mass.), wherein a helium-neon gas laser beam is projected through a transparent cell which contains silica, such as, for example, silica hydrogel particles suspended in an aqueous solution. Light rays which strike the particles are scattered through angles which are inversely proportional to the particle size. The photodetector arrant measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the metal oxide. It will be understood that other methods of measuring particle size are known in the art, and based on the disclosure set forth herein, the skilled artisan will understand how to calculate median particle size, mean particle size, and/or particle size distribution of metal oxide particles of the present invention.

In an aspect, suitable metal oxide particles such as zinc oxide particles for oral care compositions of the invention have, for example, a particle size distribution of 3 to 4 microns, or alternatively, a particle size distribution of 5 to 7 microns, alternatively, a particle size distribution of 3 to 5 microns, alternatively, a particle size distribution of 2 to 5 microns, or alternatively, a particle size distribution of 2 to 4 microns.

The oral compositions within the scope of the invention include metal oxide particles such as zinc oxide that have a median particle size that is no greater than the average diameter of a mammalian dentin tubule, such that one or more particles is/are capable of becoming lodged within the tubule, thereby effecting a reduction or elimination of perceived tooth sensitivity. Suitable particles may have, for example, a median particle size of 8 microns or less, alternatively, a median particle size of 3 to 4 microns, alternatively, a median particle size of 5 to 7 microns, alternatively, a median particle size of 3 to 5 microns, alternatively, a median particle size of 2 to 5 microns, or alternatively, a median particle size of 2 to 4 microns.

In an aspect of the invention, the metal oxide particles such as zinc oxide have a particle size which is a median particle size. In another aspect, that particle size is an average (mean) particle size. In an embodiment, the mean particle comprises at least 5%, at least 10%, at least 15%, at least 20%, at least 25%, at least 30%, at least 35%, or at least 40% of the total metal oxide particles in an oral care composition of the invention.

In an aspect of the invention, the metal oxide particles such as zinc oxide have a particle size characterized by the parameters of a median particle size of about 2 μm to about 4 μm, a d10 of about 0.5 μm to about 2 μm, and a d90 of about 5 μm to about 10 μm. As used herein, d10 refers to particles having a diameter that is 10% of the threshold of the sampled population (i.e., 10% of the population is equal to or smaller than the d10 value), and d90 refers to particles having a diameter that is 90% of the threshold of the sampled population (i.e., 90% of the population is equal to or smaller than the d90 value). In another aspect, a metal oxide such as zinc oxide has a particle size characterized by a median particle size of about 3 μm to about 5 μm, a d10 of about 1.5 μm to about 3 μm, and a d90 of about 6 μm to about 11 μm.

The metal oxide particle may be prepared by any means known or to be developed in the art, and may be surface modified, if desired, to increase the capacity of the particle to adhere to a tooth surface.

Abrasive Particulates

The oral compositions may further comprise, in addition to the metal oxide dentin tubule-occluding particles, one or more abrasive particulates. Any abrasive particulates may be used and may be selected from sodium bicarbonate, calcium phosphate (e.g., dicalcium phosphate dihydrate), calcium sulfate, precipitated calcium carbonate, silica (e.g., hydrated silica), iron oxide, aluminium oxide, perlite, plastic particles, e.g., polyethylene, and combinations thereof. In particular, the abrasive may be selected from a calcium phosphate (e.g., dicalcium phosphate dihydrate), calcium sulfate, precipitated calcium carbonate, silica (e.g., hydrated silica), calcium pyrophosphate and combinations. Any type of silica may be used, such as precipitated silicas or silica gels.

In an embodiment, the oral care composition comprises a silica that has a particle size and an amount and distribution in the oral care composition so that the silica has a dual function, and functions not only as a dentin tubule-occluding particulate but also as an abrasive particulate. Such a dual function particulate may be provided by a commercially available silica such as INEOS AC43, available in commerce from Ineos Silicas, Warrington, United Kingdom, as described elsewhere herein. In an embodiment, such a silica has a median particle size from 3 μm to 5 μm, as described in detail elsewhere herein.

Various abrasives may be used in accordance with the present invention. One class of abrasives comprises silica particles as set forth in detail herein. Another class of abrasives are powdered silicas, particularly, silica xerogels as defined in U.S. Pat. No. 3,538,230. Additionally, as set forth in U.S. Pat. No. 4,358,437, powdered forms of calcium carbonate in an abrasive form is another class of abrasives.

The compositions of the present invention may further comprise an optional abrasive useful for example as a polishing agent. Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

Polymers and Adherent Materials

The oral compositions of the invention may also include a polymeric adherent material. The polymer can assist in the retention of the metal oxide particles within the dentin tubules under salivary flow and during exposure to acidic foods and beverages.

The polymeric adherent material may be any known or to be developed in the art that attaches to the surface of a mammalian tooth and/or to the heterogeneous biofilm which also may be present on a tooth's surface. Attachment may occur by any means, such as ionic interaction, van der Waals forces, hydrophobic-hydrophilic interactions, etc. The adherent material may be, for example, any homopolymers or copolymers (hereinafter referred to collectively as a "polymers") that adhere to the surface of a tooth. Such polymers may include cellulose polymers, for example one or more hydroxyalkyl cellulose polymers, such as hydroxypropylmethyl cellulose (HPMC), hydroxyethylpropyl cellulose (HEPC), hydroxybutylmethyl cellulose (HBMC), carboxymethyl cellulose (CMC).

In one embodiment the polymeric adherent material comprises a mixture of cellulose materials, for example a mixture of two hydroxyalkyl cellulose materials having different molecular weight. The mixture typically comprises a mixture of two hydroxypropyl methyl cellulose materials of different molecular weight. In a particularly preferred embodiment, the two hydroxypropyl methyl cellulose materials comprise a mixture of HPMC materials available commercially from the Dow Chemical Company under the trade designation Methocel E5 and Methocel E50.

Modifying the polymer system can increase the strength of the film matrix to support a high loading of solids, especially zinc oxide. By rebalancing the polymer system, the present inventors discovered a method in which more actives can be loaded into the film than could be done previously. This creates a film with a higher concentration of zinc compound that can be delivered, and also reduces the amount of film needed to deliver these higher amounts. The improved higher loading zinc-containing film formula provides higher deposition onto surfaces for superior efficacy. Also, improving the film formulation to hold a higher loading of zinc compound can reduce the amount of total film needed in a product, while at the same time, delivering the same efficacy as with a lower loading of film.

The polymers may alternatively or additionally include poly (ethylene oxide) polymers (such as POLYOX from Dow Chemical), linear PVP and cross-linked PVP, PEG/PPG copolymers (such as BASF Pluracare L1220), ethylene oxide (EO)-propylene oxide (PO) block copolymers (such as polymers sold under the trade mark Pluronic available from BASF Corporation), ester gum, shellac, pressure sensitive silicone adhesives (such as BioPSA from Dow-Corning), methacrylates, or mixtures thereof. In an embodiment, a copolymer comprises (PVM/MA). In an embodiment, a copolymer comprises poly (methylvinylether/maleic anhydride). In another embodiment, a copolymer comprises poly (methylvinylether/maleic acid). In another embodiment, a copolymer comprises poly (methylvinylether/maleic acid) half esters. In another embodiment, a copolymer comprises poly (methylvinylether/maleic acid) mixed salts.

Polymers of any molecular weight may be used, including, for example molecular weights of 50,000 to 500,000, 500,000 to 2,500,000 or 2,500,000 to 10,000,000 (calculated by either number average or weight average).

In an embodiment, a copolymer of methyl vinyl ether and maleic anhydride may be used at a monomer ratio of from 1:4 to 4:1. Other polymers that may be used as adherent materials include those recited in US-A1-2006/0024246, the contents of which are incorporated herein by reference.

Commercially-available polymers may be used in the present invention. It is understood that over time, the exact size, weight and/or composition of a commercially-available polymer may change. Based on the disclosure set forth herein, the skilled artisan will understand how to determine whether such polymers are useful in the invention Compositions In an aspect of the invention, metal oxide particle-containing oral care compositions, which may optionally contain silica particles, can desensitize a tooth. In another aspect, such compositions of the invention provide tooth desensitization that is superior to conventional desensitizing dentifrices. By way of a non-limiting example, a metal oxide particle-containing dentifrice of the invention provides tooth desensitization by providing a greater desensitization than a conventional dentifrice or a conventional desensitizing dentifrice, by providing desensitization more rapidly than a conventional dentifrice or a conventional desensitizing dentifrice, or by a combination of greater desensitization and more rapid desensitization, among other effects. In an embodiment, a metal oxide particle-containing composition of the invention provides desensitization and/or superior desensitization in the absence of any other desensitizing agent. In another embodiment, a metal oxide particle-containing composition of the invention provides desensitization and/or superior desensitization, and may contain one or more additional desensitizing agents, such as silica particles, as described elsewhere herein.

The invention also encompasses methods of use and/or application of a metal oxide particle-containing desensitizing composition, which may optionally contain silica particles. In an embodiment, such a metal oxide particle-containing composition may be applied to the tooth via conventional brushing techniques (e.g., use of a toothbrush). In another embodiment, such a metal oxide particle-containing composition may be applied to the tooth via a method other than conventional brushing techniques. Other methods of application include manual application (e.g., applying a composition to a tooth using one or more fingers, rubbing onto the tooth surface, rubbing in a circular motion, etc. . . . ), or application using any known dental appliance or applicator. It will be understood, based on the disclosure set forth herein, that any method of smearing a composition onto a tooth, optionally using varying degrees of physical pressure, is encompassed by the invention.

Desensitization of a tooth according to the invention may be measured by any technique set forth herein, or any technique known to the skilled artisan.

Application of the composition to the tooth surface results in the introduction of the composition into one or more dentin tubules. The composition is applied to the teeth by any method set forth herein or known in the art.

In some embodiments, the oral care composition may include any other therapeutic, cosmetic, and/or aesthetic materials as may be desired. Examples include non-silica desensitizing agents (e.g. a nitrate salt, an arginine ester, a bicarbonate salt, potassium nitrate, an arginine-bicarbonate-phytate complex, potassium citrate, and arginine, among others), a chemical whitening agent (such as a peroxide releasing compound), an opaque whitening agent (such as hydroxyapatite) and an anticalculus agent. Other options for inclusion in the oral care composition of the invention include triclosan; stannous ion agents; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; delmopinol; octapinol; nisin; zinc ion agents; copper ion agents; essential oils; furanones; bacteriocins, ethyl lauroyl arginate, extracts of magnolia, a metal ion source, arginine bicarbonate, honkiol, magonol, ursolic acid, ursic acid, morin, extract of sea buckthorn, an enzyme, a Camellia extract, a flavonoid, a flavan, halogenated diphenyl ether, creatine, and propolis.

The oral care composition may in particular be a dentifrice composition which may be a toothpaste or a gel.

The composition according to the present invention may comprise an antimicrobial agent which may be selected from halogenated diphenyl ether (triclosan), herbal extracts or essential oils (e.g., rosemary extract, thymol, menthol, eucalyptol, methyl salicylate), bisguanide antiseptics (e.g., chlorhexidine, alexidine, or octenidine), phenolic antiseptics, hexetidine, povidone iodine, delmopinol, salifluor, sanguinarine, propolis, oxygenating agents (e.g., hydrogen peroxide, buffered sodium peroxyborate, or peroxycarbonate), cetyl pyridinium chloride, magnolia extract, magnolol, honkiol, butyl magnolol, propyl honkiol, and mixtures thereof. Anti-attachment agents such as Solrol also can be included, as well as plaque dispersing agents such as enzymes (papain, glucoamylase, etc.).

The composition according to the present invention may also comprise one or more further agents typically selected from an anti-plaque agent, a whitening agent, antibacterial agent, cleaning agent, a flavouring agent, a sweetening agent, adhesion agents, surfactants, foam modulators, abrasives, pH modifying agents, humectants, mouth feel agents, colorants, abrasive, tartar control (anticalculus) agent, fluoride ion source, saliva stimulating agent, nutrient and combinations thereof. Various components that may be added to the composition include, for example, a sweetening agent such as saccharin, or sodium saccharin, alcohols such as ethanol, fluoride ion sources such as sodium fluoride, as well as glycerine, sorbitol, propylene glycol, polyethylene glycols, Poloxomer polymers such as POLOXOMER 407, PLURONIC F108, (both available from BASF Corporation), alkyl polyglycoside (APG), polysorbate, PEG40, castor oil, menthol, and the like.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N, 2, 3-trimethyl-2-isopropylbutanamide, 3-1-menthoxypropane-1, 2-diol, cinnamaldehyde glycerol acetal (CGA), methone glycerol acetal (MGA), and mixtures thereof. One or more flavorants are optionally present in a total amount of about 0.01% to about 5%, optionally in various embodiments from about 0.05 to about 2%, from about 0.1% to about 2.5%, and from about 0.1 to about 0.5%.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%, for example about 0.01% to about 10% or about 0.1% to about 5%.

The compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

The compositions of the present invention optionally comprise a fluoride ion source and useful, for example, as an anti-caries agent. Any orally acceptable particulated fluoride ion source can be used, including potassium, sodium and ammonium fluorides and monofluorophosphates, stannous fluoride, indium fluoride, amine fluorides such as olaflur (N'-octadecyltrimethylendiamine-N,N,N'-tris(2-ethanol)-dihydrofluoride), and mixtures thereof. One or more fluoride ion sources are optionally present in an amount providing a clinically efficacious amount of soluble fluoride ion to the oral composition.

The compositions of the present invention optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

The dentifrice composition according to the present invention comprises an orally acceptable carrier in a product such as a toothpaste or a gel. As used herein, an "orally acceptable carrier" refers to a material or combination of materials that are safe for use in the compositions of the present invention, commensurate with a reasonable benefit/risk ratio.

Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable", "clinically effective", and/or "clinically efficacious" component is one that is suitable for use with humans and/or animals and is provided in an appropriate amount (a clinically efficacious amount) to provide the desired therapeutic, prophylactic, sensory, decorative, or cosmetic benefit without undue adverse side effects (such as toxicity, irritation, and allergic response) commensurate with a reasonable benefit/risk ratio.

The oral care compositions described herein may be formulated into any delivery form that permits contact of the metal oxide particles and the amino acid, and when present the polymeric adherent material, to the tooth surface. For example, the compositions may be formulated into a mouth rinse, a paste, a gel, a lozenge (dissolvable or chewable), a spray, a gum, and a film (wholly or partially dissolvable, or indissoluble). The composition may contain any conventional excipients or carriers, although these will vary depending on the dosage form or means of dosage selected. Excipients or carriers can include, for example, humectants, colorants, flavorants, glycerin, sorbitol, xylitol, and/or propylene glycol, water or other solvents, gum bases, thickening agents, surfactants, carrageenan (rich moss), xanthan gum and sodium carboxymethyl cellulose, starch, polyvinyl pyrrolidone, hydroxyethyl propyl cellulose, hydroxybutyl methyl cellulose, hydroxypropyl methyl cellulose, and hydroxyethyl cellulose and amorphous silicas.

Surfactants may be included, if desired. Examples of suitable surfactants include water-soluble salts of higher fatty acid monoglyceride monosulfates, such as the sodium salt of monosulfated monoglyceride of hydrogenated coconut oil fatty acids; higher alkyl sulfates such as sodium lauryl sulfate; alkyl aryl sulfonates such as sodium dodecyl benzene sulfonate; higher alkyl sulfoacetates, such as sodium lauryl sulfoacetate; higher fatty acid esters of 1,2-dihydroxypropane sulfonate; and the substantially saturated higher aliphatic acyl amides of lower aliphatic amino carboxylic compounds, such as those having 12-16 carbons in the fatty acid, alkyl or acyl radicals; and the like. Examples of the last mentioned amides include N-lauryl sarcosine, and the sodium, potassium and ethanolamine salts of N-lauryl, N-myristoyl, or N-palmitoyl sarcosine. Others include, for example, nonanionic polyoxyethylene surfactants, such as Polyoxamer 407, Steareth 30, Polysorbate 20, and castor oil; and amphoteric surfactants, such as cocamidopropyl betaine (tegobaine), and cocamidopropyl betaine lauryl glucoside; condensation products of ethylene oxide with various hydrogen containing compounds that are reactive therewith and have long hydrocarbon chains (e.g., aliphatic chains of from 12 to 20 carbon atoms), which condensation products (ethoxamers) contain hydrophilic polyoxyethylene moieties, such as condensation products of poly (ethylene oxide) with fatty acids, fatty, alcohols, fatty amides and other fatty moieties, and with propylene oxide and polypropylene oxides.

In an embodiment, the oral composition includes a surfactant system that is sodium laurel sulfate (SLS) and cocamidopropyl betaine.

The oral care composition of the invention may be prepared by any means known in the art. For example, preparation methods for dentifrices are well known, for example, as described in U.S. Pat. Nos. 3,966,863; 3,980, 767; 4,328,205; and 4,358,437, the contents of which are incorporated herein by reference. In general, any humectant (e.g., glycerin, sorbitol, propylene glycol, and/or polyethylene glycol) is dispersed in water in a conventional mixer under agitation. Into that dispersion are added the thickeners, such as carboxylmethyl cellulose (CMC), carrageenan, or xanthan gum; any anionic polycarboxylate; any salts, such as sodium fluoride anticaries agents; and any sweeteners.

The resultant mixture is agitated until a homogeneous gel phase is formed. Into the gel phase are added any pigments utilized, such as $TiO_2$, and additionally any acid or base required to adjust the pH of the composition. These ingredients are mixed until a homogeneous phase is obtained.

The mixture is then transferred to a high speed/vacuum mixer, wherein the surfactant ingredients are added to the mixture. The metal oxide particles and any silica particles utilized are added subsequently. Any water insoluble agents, such as triclosan, are solubilized in the flavor oils to be included in the dentifrice, and that solution is added along with the surfactants to the mixture, which is then mixed at high speed in the range from 5 to 30 minutes, under a vacuum of 20 to 50 mm of Hg. The resultant product is a homogeneous, semi-solid, extrudable paste or gel product.

Methods of Use

The oral care, e.g. dentifrice, composition according to the present invention may be administered to or applied to a human or other animal subject. The composition is suitable for administration or application to the oral cavity of a human or animal subject.

The invention also includes within its scope several related methods. For example, the invention includes within its scope methods of reducing and methods of occluding a dentin tubule of a mammalian tooth, methods of protecting dentin from acid-mediated degradation, and methods of reducing dental sensitivity.

Each of these methods includes the steps of applying any of the compositions described above to the tooth surface. Application may be carried out by any method, so long as the adherent material and the particles are placed in contact with the tooth surface. Application may be accomplished by brushing, flossing, prophylaxis, irrigating, wiping, rinsing (lavage of oral cavity), foam/gel and in-tray application, masticating, spraying, painting, etc., or applied by film or strip.

Dental sensitivity may be reduced according to a method of the invention by applying a composition of the invention to a tooth surface. A composition may be applied using a traditional method, as described in detail elsewhere herein, or by any appliance or applicator, whether or not typically associated with dental use. In an embodiment, one or more human fingers is used to apply a dental sensitivity-reducing composition to one or more teeth. A finger can be used to smear the composition on the surface of a tooth, or to otherwise apply the composition to the surface of a tooth.

Alternatively, the invention includes methods to increase or maintain the systemic health of a mammal by applying a composite to an oral surface (both hard and soft tissues of the oral cavity). The composition for use in this method may be any described above, provided that it contains at least one of triclosan; triclosan monophosphate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; delmopinol; octapinol; nisin; zinc ion agent; copper ion agent; essential oils; furanones; bacteriocins, ethyl lauroyl arginate, extracts of magnolia, a metal ion source, arginine bicarbonate, honokiol, magonol, ursolic acid, ursic acid, morin, extract of sea buckthorn, a peroxide, an enzyme, a Camellia extract, a flavonoid, a flavan, halogenated diphenyl ether, creatine, and propolis. The application may be at least once a day, although up to five times per day may be preferred, and may be carried out over a duration of time, e.g., one week, up to one year, up to three years or for a lifetime.

Various embodiments now will be described with reference to the following non-limiting examples

EXAMPLES

Example 1

A dentifrice composition having the formula of Table 1 was prepared. The compositions used in the Examples and Comparative Examples had varying amounts of zinc oxide (varying from 0 to 2 wt %) and of amino acid (varying from 0 to 5 wt %). For Example 1, the dentifrice composition comprised 1 wt % zinc oxide powder, the ZnO being encapsulated, at a 50 wt % loading, into a polymer film, in particular into a polymer film comprising a combination of two different molecular weight HPMC materials, comprising Methocel E5 and Methocel E50. The combined zinc oxide/polymer film comprised 1 wt % ZnO and 1 wt % polymer film, each weight being based on the total weight of the composition. For Example 1, the dentifrice composition also comprised 4.3 wt % L-arginine.

TABLE 1

Dentifrice Composition

| Ingredient | % w/w |
| --- | --- |
| Sorbitol | Q.S. |
| Water | 11.944 |
| Silica-Zeodent 105 | 10.000 |
| Silica-Zeodent 114 | 10.000 |
| Polyethylene Glycol 600 | 3.000 |
| Silica-Zeodent 165 | 2.750 |
| Source of Zinc oxide (ZnO in polymer film) | 0-2 |
| Sodium Laury 1 Sulfate | 1.500 |
| Cocamidopropyl Betaine | 1.250 |
| Flavor | 1.150 |
| Titanium Dioxide | 0.750 |
| Sodium CM-Type 7MF | 0.650 |
| Amino acid (L-arginine) | 0-5 |
| Sodium Saccharin | 0.270 |
| Sodium Fluoride | 0.243 |

To measure the delivery of zinc to hydroxyapatite, the dentifrice was diluted 1 part by weight dentifrice to 2 parts by weight water and stirred to disperse the dentifrice. Next a saliva coated hydroxyapatite disk was added to this slurry. The disk was treated with the slurry for 10 minutes and then rinsed three times with five mL of water. The disk was then digested with nitric acid and total zinc measured by atomic absorption spectroscopy.

The zinc uptake data from the dentifrice formula of Example 1 containing L-arginine and zinc oxide delivered from a polymer film when used as a slurry are provided in Table 2.

It may be seen from Example 1 that the zinc uptake was significant.

TABLE 2

Zinc uptake onto hydroxyapatite from a dentifrice slurry.

| Chelating molecule | Zinc uptake (ug/disk) |
| --- | --- |
| Comparative Example 1-None | 14.1 ± 1.1 |
| Example 1-L-arginine | 103.5 ± 10.6 |

Comparative Example 1

For Comparative Example 1, the dentifrice composition having the formula of Table 1 was prepared which comprised (like Example 1) 1 wt % ZnO encapsulated in a polymer film, but was modified as compared to Example 1 in that no chelating molecule, such a L-arginine, was present.

The result is also shown in table 2. It may be seen from Comparative Example 1 that the zinc uptake was significantly lower, nearly an order of magnitude lower, than for Example 1.

A comparison of Example 1 and Comparative Example 1 shows that the chelating agent enhances delivery of the zinc oxide to the dentin surface, in particular when employed in combination with a polymer film.

Examples 2 to 7 and Comparative Example 2

Example 1 was repeated except that for Example 2 a different amount of L-arginine was used and for Examples 3 to 7 different amounts of different amino acids were used. In addition, for Examples 2 to 7 all of the formulas contained 1% ZnO as a powder, and no polymer film as for Example 1 was present. Examples 2 to 7 employed a 1.4:1 molar ratio of the respective amino acid to the ZnO powder. For Comparative Example 2, again no amino acid was present and the ZnO was present as a powder.

The results of the zinc uptake test as described above with respect to Example 1 are summarised in Table 3. The zinc uptake data from dentifrice formulas of Examples 2 to 7 containing zinc oxide powder and a variety of amino acids are shown in Table 3, as is the result from Comparative Example 2.

TABLE 3

| Zinc uptake onto hydroxyapatite from a dentifrice slurry. Chelating molecule | Zinc uptake (ug/disk) |
| --- | --- |
| Comparative Example 2-None | 5.9 ± 0.4 |
| Example 2-L-arginine | 99.0 ± 7.0 |
| Example 3-L-lysine | 121.5 ± 7.8 |
| Example 4-Serine | 170.1 ± 8.0 |
| Example 5-Cysteine | 188.8 ± 24.4 |
| Example 6-Isoleucine | 94.7 ± 2.0 |
| Example 7-Glutamic acid | 95.3 ± 7.3 |

A comparison of Examples 1 and 2 in both Tables 2 and 3 confirms that zinc uptake is significantly increased by the addition of L-arginine to the dentifrice and the effect is observed whether the zinc oxide is added to the dentifrice encapsulated in a polymer film (Example 1) or as a powder (Example 2). Table 3 highlights that zinc uptake can be increased by a variety of amino acids.

The results of these Examples and Comparative Examples demonstrate that amino acids can improve delivery of insoluble zinc oxide to a surface similar to that found in the oral cavity. The increased delivery of zinc oxide should improve the antibacterial benefits associated with an increase in zinc.

These Examples evidence a number of amino acids which appear to be able to deliver zinc to surfaces in the oral cavity. Additional amino acids such as leucine, lysine, alanine, asparagine, aspartate, phenylalanine, glutamate, threonine, glutamine, tryptophan, glycine, valine, praline, tyrosine, and histidine could also be used. The delivery of other metal oxide particles, such as stannous or copper oxide, to surfaces in the oral cavity may also be improved by combination with amino acids.

Example 3

Example 3 was carried out to evaluate the occlusion efficacy of a dentifrice formula including an amino acid as a chelator for zinc oxide.

For Example 3, a dentifrice composition having the formula of Table 1 was prepared which comprised 1 wt % zinc oxide powder (as Example 2) and 3 wt % of amino acid, which comprised L-arginine.

To evaluate the occlusion efficacy of the dentifrice formulas, dentin disks were prepared from human molars. The molars were sliced, sanded, and polished. Finally, the disks were etched with 6 wt % citric acid and sonicated to open the tubules on the dentin surface. Each disk was brushed for 1 minute and 30 seconds with a mechanical toothbrush and a 1:2 by weight water to dentifrice slurry. After brushing, the disk was rinsed for 15 seconds with water and then stored in a phosphate buffer solution for 15 minutes. This treatment cycle was repeated 7 times per disk. After the seventh treatment, the disks were examined using a confocal microscope to image the degree of surface coverage by the dentifrice product. The disks were then exposed to 1 min acid challenges (using a commercial cola carbonated beverage) and examined after each treatment to evaluate the amount of product remaining in the dentin tubules. The results of this study are shown in FIG. 1.

It may be seen for Example 3 that after 7 brushing cycles there was good occlusion of the dentin tubules. After 12 subsequent acid challenge cycles using cola, there was still good occlusion of the dentin tubules.

Comparative Example 3

For Comparative Example 3, the dentifrice composition having the formula of Example 3 (i.e. 1 wt % ZnO powder) but omitting the L-arginine was prepared. This dentifrice was subjected to the same occlusion efficacy testing as Example 3, and the result is also shown in FIG. 1. It may be seen for Comparative Example 3 that after 7 brushing cycles there was poor occlusion of the dentin tubules. After 12 subsequent acid challenge cycles using cola, there was even worse occlusion of the dentin tubules.

A comparison of Example 3 and Comparative Example 3 shows that the metal oxide particles, in particular zinc oxide particles, provide good dentin occlusion when employed in combination with an amino acid such as L-arginine as a chelator.

Without being bound by any theory, it is believed that the amino acid is likely to improve the adhesion of ZnO inside dentin tubules, and to other surfaces in the oral cavity, by forming a bridge between zinc oxide and the dentin. The negatively charged carboxylate group on the amino acid is suspected to bind to the zinc oxide (due to the existence of a positive zeta potential at pH<9 for the zinc oxide, as disclosed in an article entitled "The effect of pH on the corrosion inhibition of zinc pigments by phenol derivatives", by at B. Muller and W. Klager, Corrosion Science, 38 (1996), pages. 1869-1875), with the positively charged group correspondingly binding to the surface of the dentin. All amino acids are zwitterionic at physiological pH, and so it is believed that the amino acid may be able to bind a charged particle to charged surfaces in the oral cavity. The charge and functionality of the R-group of the amino acid varies among amino acids; however from the current studies by the inventors, the charge/functionality on the R-group appears not to have a significant impact on zinc uptake to hydroxyapatite surfaces, as evidenced by the results of Table 3.

As shown in FIG. 1, it has been found by the present inventors that the increased delivery of zinc oxide to dentin by L-arginine provides occlusion of dentin tubules which is more resistant to acid attack than zinc oxide alone. This is an additional potential benefit provided by the zinc oxide/amino acid system as occlusion of dentin tubules is associated with hypersensitivity relief.

The invention claimed is:

1. An oral care composition comprising:
    an orally acceptable vehicle;
    a source of metal oxide particles, wherein said metal oxide particles have a median particle size of from 1 to 7 microns;
    one or more amino acids capable of chelating said metal oxide particles selected from arginine, L-arginine, cysteine, leucine, isoleucine, lysine, L-lysine and serine;
    an abrasive particulate selected from calcium phosphate, calcium sulphate, precipitated calcium carbonate, silica, calcium pyrophosphate, and combinations thereof;
    wherein the metal oxide comprises zinc oxide, wherein the metal oxide is encapsulated in a polymeric adherent material, and wherein the polymeric adherent material comprises a hydroxylalkyl cellulose polymer; and
    wherein the hydroxyalkyl cellulose polymer is selected from hydroxypropylmethyl cellulose (HPMC), hydroxyethylpropyl cellulose (HEPC), hydroxybutylmethyl cellulose (HBMC), and carboxymethyl cellulose (CMC); and
    wherein the oral care composition is in the form of a toothpaste.

2. The oral care composition according to claim 1 wherein the metal oxide particles have a median particle size of 5 microns or less.

3. The oral care composition according to claim 1 wherein the metal oxide particles have a particle size distribution of 3 to 4 microns, a particle size distribution of 5 to 7 microns, a particle size distribution of 3 to 5 microns, a particle size distribution of 2 to 5 microns, or a particle size distribution of 2 to 4 microns.

4. The oral care composition according to claim 1 wherein the metal oxide particles are present in an amount of up to 5% by weight, based on the total weight of the oral care composition.

5. The oral care composition according to claim 3 wherein the metal oxide particles are present in an amount of from 0.5 to 2% by weight, based on the total weight of the oral care composition.

6. The oral care composition according to claim 1 wherein the source of metal oxide particles is selected from a powder, a nanoparticle solution; a nanoparticle suspension; a capsule; and a bead.

7. The oral care composition according to claim 1 wherein at least one of said one or more amino acids is L-arginine.

8. The oral care composition according to claim 1 wherein at least one of said one or more amino acids is present in an amount of up to 5% by weight, based on the total weight of the oral care composition.

9. The oral care composition according to claim 7 wherein at least one of said one or more amino acids is present in an amount of from 0.5 to 5% by weight, based on the total weight of the oral care composition.

10. The oral care composition according to claim 8 wherein at least one of said one or more amino acids is present in an amount of from 2.5 to 4.5% by weight, based on the total weight of the oral care composition.

11. The oral care composition according to claim 1 wherein the polymeric adherent material comprises a mixture of two hydroxyalkyl cellulose polymers having different molecular weights and the metal oxide comprises zinc oxide which is encapsulated in the mixture of two hydroxyalkyl cellulose polymers.

12. A method of reducing dental sensitivity comprising applying to the surface of a mammalian tooth an oral care composition of claim 1.

13. A method of protecting dental surfaces from acid-mediated degradation, comprising applying to the surface of a mammalian tooth an oral care composition of claim 1.

14. A method of maintaining or increasing the systemic health of a mammal comprising applying a composition to an oral surface of a mammal at least once a day for a duration of time, wherein the composition comprises:
  a. an oral care composition of claim 1, and
  b. an agent selected from triclosan; triclosan monophosphate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4ethylpyridinium chloride (TDEPC); octenidine; delmopinol; octapinol; nisin; zinc ion agent; copper ion agent; essential oils; furanones; bacteriocins, ethyllauroyl arginate, extracts of magnolia, a metal ion source, fluoride, stannous ions, arginine bicarbonate, honokiol, magonol, ursolic acid, ursic acid, morn, extract of sea buckthorn, a peroxide, an enzyme, a Camellia extract, a flavonoid, a flavan, halogenated diphenyl ether, creative, and propolis.

15. A method of occluding a dentin tubule within the surface of a mammalian tooth comprising applying to the tooth surface a composition according to claim 1.

16. An oral care composition according to claim 1 and further comprising an agent selected from triclosan; triclosan monophosphate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4ethylpyridinium chloride (TDEPC); octenidine; delmopinol; octapinol; nisin; zinc ion agent; copper ion agent; essential oils; furanones; bacteriocins, ethyllauroyl arginate, extracts of magnolia, a metal ion source, fluoride, stannous ions, arginine bicarbonate, honokiol, magonol, ursolic acid, ursic acid, morn, extract of sea buckthorn, a peroxide, an enzyme, a Camellia extract, a flavonoid, a flavan, halogenated diphenyl ether, creative, and propolis, for use in a method of maintaining or increasing the systemic health of a mammal.

17. The oral care composition according to claim 11 wherein the metal oxide particles are present in an amount of from 0.5 to 2% by weight, based on the total weight of the oral care composition.

18. The oral care composition according to claim 17 wherein at least one of said one or more amino acids is present in an amount of from 0.5 to 5% by weight, based on the total weight of the oral care composition.

* * * * *